US010266823B2

(12) United States Patent
Juliano et al.

(10) Patent No.: US 10,266,823 B2
(45) Date of Patent: Apr. 23, 2019

(54) SMALL MOLECULES THAT ENHANCE THE ACTIVITY OF OLIGONUCLEOTIDES

(71) Applicants: The University of North Carolina at Chapel Hill, Chapel Hill, NC (US); Southern Research Institute, Birmingham, AL (US)

(72) Inventors: Rudolph Juliano, Chapel Hill, NC (US); William P. Janzen, Chapel Hill, NC (US); Joseph A. Maddry, Birmingham, AL (US); Canhong Cao, Chapel Hill, NC (US); Xin Ming, Chapel Hill, NC (US); Bing Yang, Chapel Hill, NC (US)

(73) Assignees: The University of North Carolina at Chapel Hill, Chapel Hill, NC (US); Southern Research Institute, Birmingham, AL (US)

( * ) Notice: Subject to any disclaimer, the term of this patent is extended or adjusted under 35 U.S.C. 154(b) by 0 days.

(21) Appl. No.: 15/318,260

(22) PCT Filed: Jun. 26, 2015

(86) PCT No.: PCT/US2015/038058
§ 371 (c)(1),
(2) Date: Dec. 12, 2016

(87) PCT Pub. No.: WO2016/003816
PCT Pub. Date: Jan. 7, 2016

(65) Prior Publication Data
US 2017/0130222 A1    May 11, 2017

Related U.S. Application Data

(60) Provisional application No. 62/019,549, filed on Jul. 1, 2014.

(51) Int. Cl.
| | |
|---|---|
| *A61K 48/00* | (2006.01) |
| *C07H 21/02* | (2006.01) |
| *C07H 21/04* | (2006.01) |
| *C12N 15/113* | (2010.01) |
| *A61K 31/4985* | (2006.01) |
| *A61K 31/7088* | (2006.01) |
| *C12N 15/11* | (2006.01) |

(52) U.S. Cl.
CPC ........ *C12N 15/113* (2013.01); *A61K 31/4985* (2013.01); *A61K 31/7088* (2013.01); *C12N 15/111* (2013.01); *C12N 2310/11* (2013.01); *C12N 2310/14* (2013.01); *C12N 2310/315* (2013.01); *C12N 2310/321* (2013.01); *C12N 2310/346* (2013.01); *C12N 2310/351* (2013.01); *C12N 2320/32* (2013.01)

(58) Field of Classification Search
CPC .. C12N 15/113; C12N 2310/11; A61K 31/713
See application file for complete search history.

(56) References Cited

U.S. PATENT DOCUMENTS

| | | | |
|---|---|---|---|
| 9,534,220 B2 * | 1/2017 | Geller et al. | ......... C12N 15/113 |
| 2013/0085139 A1 * | 4/2013 | Dickson et al. | ... C12N 2310/11 |

FOREIGN PATENT DOCUMENTS

WO    WO 2013/123217 A1    8/2013

OTHER PUBLICATIONS

Notification Concerning Transmittal of International Preliminary Report on Patentability corresponding to International Application No. PCT/US2015/038058 dated Jan. 12, 2017.
Mathew et al. "Novel pyridopyrazine and pyrimidothiazine derivatives as FtsZ inhibitors", *Bioorganic & Medicinal Chemistry* 19:7120-7128 (2011).
Ming et al. "The small molecule Restro-1 enhances the pharmacological actions of antisense and splice switching oligonucleotides", *Nucleic Acids Research* 41(6):3673-3687 (2013).
Yang et al. "High-throughput screening identifies small molecules that enhance the pharmacological effects of oligonucleotides", *Nucleic Acids Research* 43(4):1987-1996 (2015).
Notification of Transmittal of the International Search Report and the Written Opinion of the International Searching Authorty, or the Declaration corresponding to International Application No. PCT/US2015/038058 dated Oct. 15, 2015.

* cited by examiner

*Primary Examiner* — Amy H Bowman
(74) *Attorney, Agent, or Firm* — Myers Bigel, P.A.

(57) ABSTRACT

Methods of administering an oligonucleotide of interest into a cell in vitro or in vivo are described. In the methods, a small organic compound active agent is concurrently administered to the cell in an amount effective to increase the delivery of the oligonucleotide into the cell, and/or increase the activity of said oligonucleotide in the cell. Compositions useful for carrying out the method are also described.

20 Claims, 3 Drawing Sheets
Specification includes a Sequence Listing.

SMALL MOLECULES THAT ENHANCE THE ACTIVITY OF OLIGONUCLEOTIDES

RELATED APPLICATIONS

This application is a 35 U.S.C. § 371 national phase application PCT/US2015/038058, filed Jun. 26, 2015, which claims the benefit of United States provisional patent application Ser. No. 62/019,549, filed Jul. 1, 2014, the entire contents of each of which is incorporated by reference herein in its entirety.

GOVERNMENT SUPPORT

This invention was made with Government support under grant number RO1CA151964 and R21CA170332 from the National Institutes of Health. The U.S. Government has certain rights to this invention.

STATEMENT REGARDING ELECTRONIC FILINGS OF A SEQUENCE LISTING

A Sequence Listing in ASCII text format, submitted, under 37 C.F.R. § 1.821, entitled 5470-712_ST25.txt, 1,657 bytes in size, generated on Dec. 9, 2016 and filed via EFS-Web, is provided in lieu of a paper copy. This Sequence Listing is hereby incorporated by reference into the specification for its disclosures.

FIELD OF THE INVENTION

This application concerns methods, compounds and compositions for delivering nucleic acids to a cell of interest.

BACKGROUND OF THE INVENTION

There have been numerous clinical trials involving various types of oligonucleotides including 'classic' antisense (AS), siRNAs, and splice switching oligonucleotides (SSOs), testifying to the immense interest in this broad therapeutic approach. Nonetheless, oligonucleotide-based therapies face a key problem regarding the inefficient access of oligonucleotides to their sites of action in the nucleus or cytosol of tissue cells. This problem has meant that large doses must be given to attain therapeutic effects thus risking drug-related toxicities, or that complex delivery systems such as cationic lipid or polymer nanoparticles must be used thus creating toxicity and biodistribution problems associated with the delivery system itself. Therefore it is clear that the discovery of alternative strategies to enhance the access of oligonucleotides to their intracellular targets will have substantial value for oligonucleotide-based pharmacology and therapeutics.

Oligonucleotides are usually internalized via endocytosis and then traffic through various membrane-bound vesicular compartments. Cells employ multiple distinct endocytotic uptake mechanisms including the 'classic' clathrin pit pathway, the caveolar pathway, one or more caveolin and clathrin-independent pathways, and macropinocytosis. Initial uptake is followed by trafficking into a variety of endomembrane compartments including early/sorting endosomes, late endosomes/multi-vesicular bodies, lysosomes, and the trans-Golgi network (TGN). Most of the oligonucleotide accumulated in cells remains sequestered in endomembrane vesicles and is pharmacologically inert, but a small fraction escapes to the cytosol and nucleus to permit activity. Recently we, and others, have found that the route of uptake and pathway of intracellular trafficking can have a strong effect on the pharmacological activity of the oligonucleotide; there are productive and less productive pathways. These observations suggest that if it were possible to influence the intracellular trafficking of oligonucleotides, and their release from endomembrane compartments, one might be able to substantially enhance their pharmacological effects and/or the physiological activity thereof. See, e.g., R. Juliano et al., Small Molecules that Enhance the Activity of Oligonucleotides, PCT Application WO 2013/123217 (22 Aug. 2013).

SUMMARY OF THE INVENTION

A first aspect of the invention is, in a method of administering an oligonucleotide of interest into a cell, the improvement comprising: concurrently administering an active agent as described herein to said cell in an amount effective to increase the delivery and/or increase the activity of said oligonucleotide in said cell.

In some embodiments, the cell is a mammalian cell.

In some embodiments, the method is carried out in vitro or in vivo.

In some embodiments, the method is carried out by administering said oligonucleotide to a subject in need thereof, and concurrently administering said active agent to said subject.

In some embodiments, the active agent is administered after said oligonucleotide.

In some embodiments, the oligonucleotide is single stranded.

In some embodiments, the oligonucleotide is from 2, 4, 6 or 8 to 100 or 200 nucleotides in length.

In some embodiments, the oligonucleotide is negatively charged.

In some embodiments, the oligonucleotide is an antisense oligonucleotide.

In some embodiments, the oligonucleotide is a splice switching oligonucleotide (SSO).

A further aspect of the invention is the use of an active agent as described herein for carrying out a method as described herein, or for the preparation of a medicament for carrying out a method as described herein.

A further aspect of the invention is the use of an oligonucleotide as described herein for carrying out a method as described herein, or for the preparation of a medicament for carrying out a method as described herein.

A further aspect of the invention is a composition comprising, consisting of or consisting essentially of: (a) an oligonucleotide as described herein; and (b) an active agent as described herein, in combination in (c) a pharmaceutically acceptable carrier.

Means+/−SE. N=3. Mismatched controls were at baseline level on this scale and are not shown.

Figure 1A:
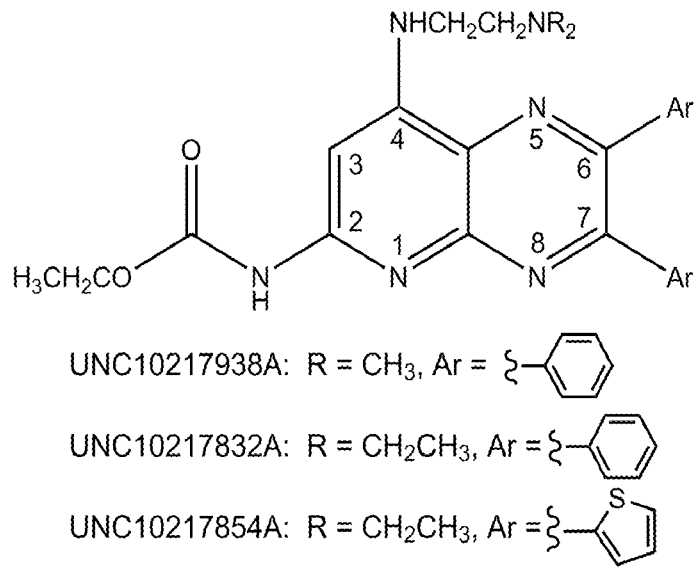
FIG. 1A. Structures of hit compounds from high throughput screening.
Figure 1B:
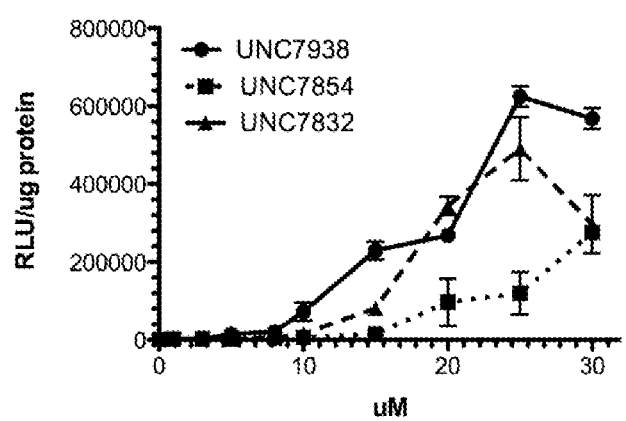
FIG. 1B. SSO Dose-response of hit compounds. Selected hits were examined for their ability to enhance splice correction by SSO623 in the HeLa Luc 705 cell system. Cells were incubated in 24 well plates with 100 nM 623 or its mismatched control (MM) for 16 h in DMEM+10% FBS, rinsed, and then treated with various concentrations of the hit compounds, or with 100 uM Retro-1, for 2 h. The cells were then rinsed and incubation continued for an additional 4 h in DMEM+10% FBS. Cells were rinsed twice in PBS and luciferase activity (RLU) and cell protein determined.
Figure 1C:
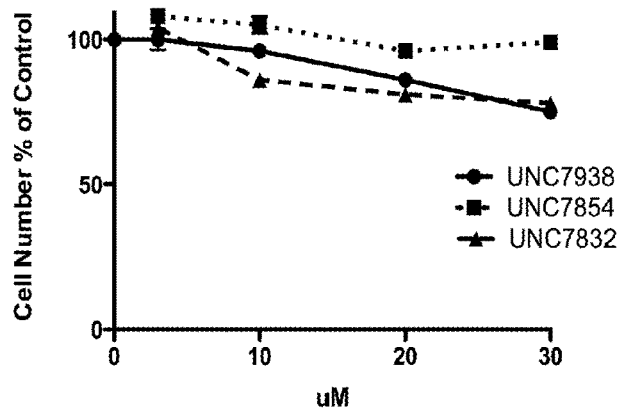

FIG. 1C. Cytotoxicity of hit compounds. Cells were exposed to hit compounds as in 1b then incubated for 24 h in DMEM plus 10% FBS and tested using the Alamar Blue cytotoxicity assay. Means+/−SE. N=3.

Figure 2:
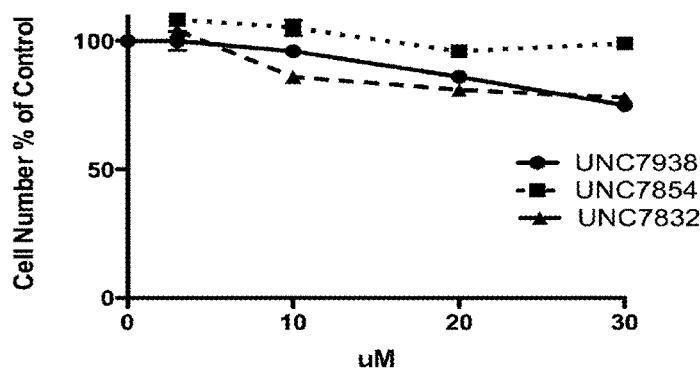

FIG. 2. Effects on Receptor-Targeted oligonucleotides. A375Luc705 cells were treated with 100 nM RGD-SSO-albumin conjugate for 16 h and subsequently treated with Retro-1 (100 uM) or 7938 (5, 10 uM) for 2 h. After removal of the compound the cells were incubated for a further 24 h and then assayed for luciferase and cell protein. (A) Control; (B) RGD-SSO conjugate only; (C) RGD-SSO conjugate plus Retrol; (D) RGD-SSO conjugate plus 5 uM 7938; (E) RGD-SSO conjugate plus 10 uM 7938. Means+/−SE. N=3.

Figure 3A:
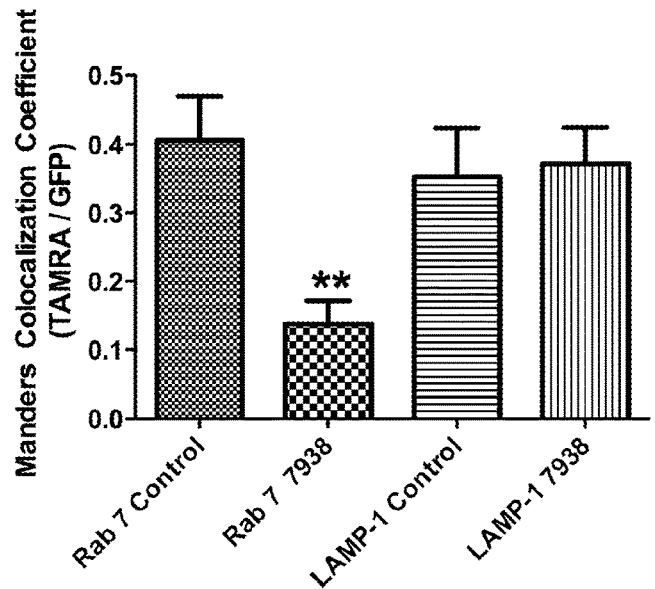

FIG. 3A: Effects on Cell Morphology and Subcellular Distribution of Oligonucleotide: Quantitation of Colocalization. HeLa cells were transfected with baculovirus expression vectors for GFP-Rab7a (late endosome marker) or GFP-LAMP-1 (lysosome marker). The cells were then incubated with 300 nM SSO 623-TAMRA for 16 h. Cells were then treated with 10 uM 7938 for 1 h or maintained as controls. Live cells were imaged using a confocal microscope with environmental stage. Co-localization of GFP and TAMRA oligonucleotide was quantitated using the Image J Coloc2 plug-in and expressed as the Manders correlation coefficient. Individual cells were analyzed and the data summated. Means and standard errors shown. N=9-20. ** represents p<0.002 compared to Rab 7 control.

Figure 3B:
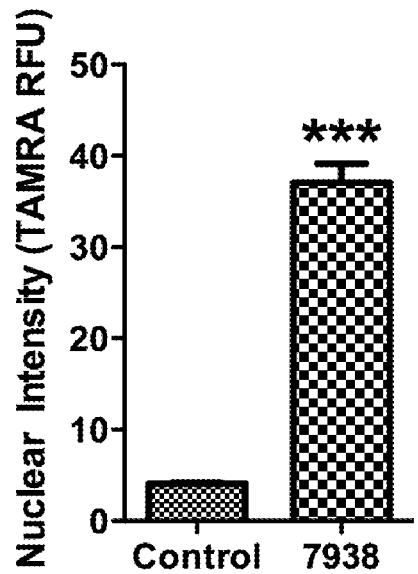

FIG. 3B. Effects on Cell Morphology and Subcellular Distribution of Oligonucleotide: Nuclear Accumulation. TAMRA fluorescence intensity in the nucleus was quantitated using Image J. Means and standard errors shown. N=55-70. *** represents p<0.001 compared to Control.

Figure 4:
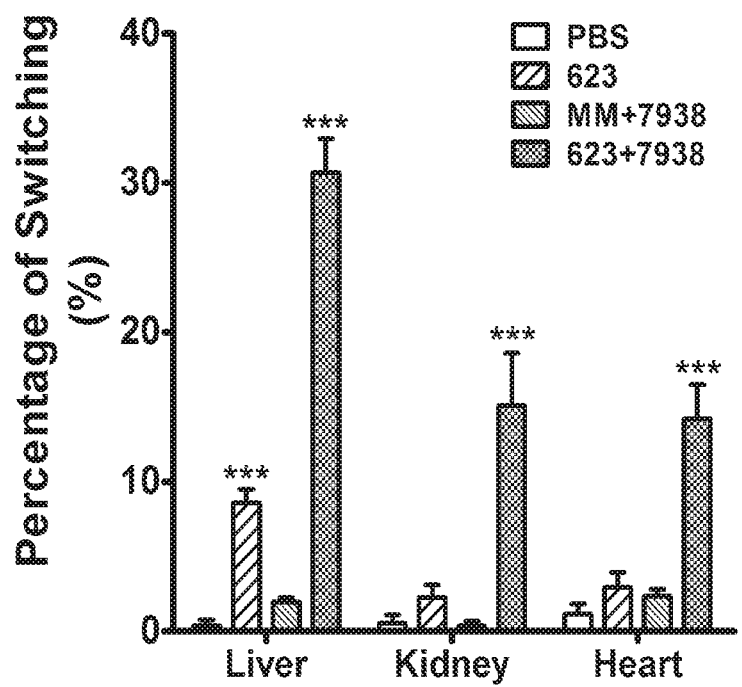

FIG. 4. In vivo effects: Quantitation of RT-PCR. Gel bands were quantitated using a Typhoon imaging system. Percent of switching is the ratio of lower band to upper band ×100. *** difference from PBS control significant at the 0.001 level.

DETAILED DESCRIPTION OF THE PREFERRED EMBODIMENTS

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents and other references mentioned herein are incorporated by reference in their entirety.

1. DEFINITIONS

"Subjects" with which the present invention is concerned are primarily human subjects, but the invention may also be carried out on animal subjects, particularly mammalian subjects such as dogs, cats, livestock and horses for veterinary purposes. While subjects may be of any suitable age, the subjects are in some embodiments neonatal, infant, juvenile, adolescent, adult, or geriatric subjects.

"Treat" as used herein refers to any type of treatment that imparts a benefit to a subject or patient afflicted with a condition, such as by delaying the progression of a disorder, delaying the severity of at least one symptom of a disorder, etc.

"Pharmaceutically acceptable" as used herein means that the compound or composition is suitable for administration to a subject to achieve the treatments described herein, without unduly deleterious side effects in light of the severity of the disease and necessity of the treatment.

"Concurrently" as used herein means sufficiently close in time to produce a combined effect (that is, concurrently may be simultaneously, or it may be two or more events occurring sequentially in time, typically within a short time period before or after each other). Thus active agents or retro compounds may be administered before, simultaneously with, or after said oligonucleotide, so long as the intended effect on the oligonucleotide activity or delivery is achieved.

"Enhance the delivery" as used herein refers to any administration of a intracellular trafficking route modulator effective to increase the cytosolic and/or nuclear concentration, accumulation, and/or half-life of the oligonucleotide (e.g., as compared to that found without concurrent administration of the active agents described herein)

"Enhance the activity" as used herein refers to, for example, any administration of a intracellular trafficking route modulator effective to increase the activity of an antisense oligonucleotide (ASO) that acts on pre-mRNA via RNase H in the nucleus, on a siRNA that acts via the RISC complex in the cytosol, and/or (for SSOs) increase the alteration of pre-mRNA splicing, as reflected by an increase in the desired splice variant (which can be measured by any suitable technique, such as by a reporter gene readout; amelioration or treatment of symptoms in a subject, etc.), or (for antisense oligonucleotides) reduced levels of the corresponding target mRNA and/or protein, or of an siRNA (which can be measured by any suitable technique, such by flow cytometry for protein levels, treatment or amelioration of symptoms in a subject, etc.) (e.g., as compared to that found without concurrent administration of the active agents described herein).

"Oligonucleotide" or "Oligo" herein refers to polymers of deoxyribonucleotides or ribonucleotides in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid. Examples of such analogs include, without limitation, phosphorothioates, phosphoramidates, methyl phosphonates, chiral-methyl phosphonates, 2-O-methyl ribonucleotides, peptide-nucleic acids (PNAs). The oligonucleotide may be of any suitable length, e.g., from 2, 3, 4, 5, 6, 8 or 10 nucleotides in length, up to 50, 60, 80, 100, 150 or 200 nucleotides in length, or more. Suitable oligonucleotides include, but are not limited to, short hairpin RNA (shRNA), microRNAs, antisense oligonucleotides (including splice switching oligonucleotides or "SSOs"), small double stranded interference RNA (siRNA)s, and ribozymes.

Antisense oligonucleotides are known. Examples include, but are not limited to, those described in U.S. Pat. Nos. 8,067,571; 7,910,563; 7,563,778; 7,393,951; 7,307,069; 6,972,171; 6,417,169; 6,339,071; 6,312,900; 6,277,832; 5,985,558; and many others.

"Splice switching oligonucleotides" (or "SSOs") are known and described in, for example, U.S. Pat. Nos. 8,067, 569; 7,888,012; 7,884,194; 7,785,834; 6,727,355; 6,653, 467; 6,653,466; and 5,976,879, and in US Patent Application No. 20100130591 to Sazani and Kole (May 27, 2010), the disclosures of all of which are incorporated by reference herein in their entirety. See also J. Bauman et al., *Oligonucleotides* 19, 1-14 (2009); P. Sazani and R. Kole, *J. Clin. Invest* 12, 481-486 (2003).

2. ACTIVE AGENTS

Active agents of the present invention are, in general, compounds of Formula I:

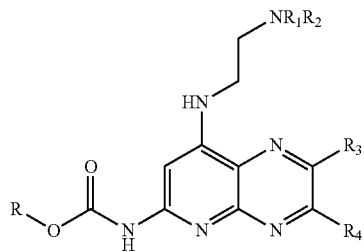

(I)

wherein:

R is ethyl or a linking group (preferably ethyl);

$R_1$ is methyl or a linking group (preferably methyl);

$R_2$ is methyl;

$R_3$ and $R_4$ are each independently H, lower alkyl; lower alkoxy, halo, amino, aryl, or heteroaryl;

or a pharmaceutically acceptable salt thereof.

Examples of the foregoing include, but are not limited to:

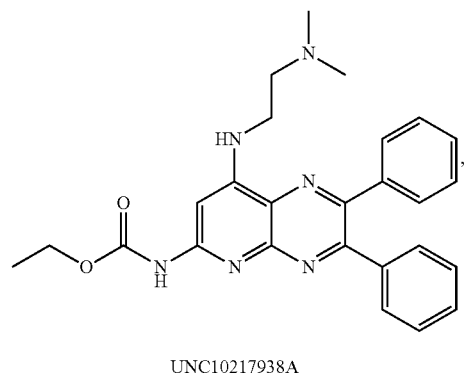

UNC10217938A

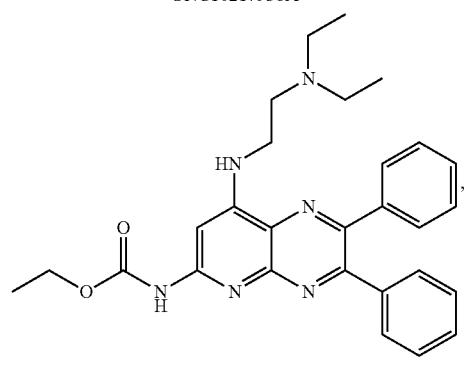

UNC10217832

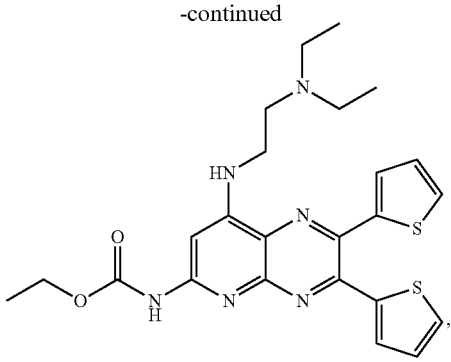

UNC10217854 and pharmaceutically acceptable salts thereof.

Compounds as described above can be made in accordance with known techniques or variations thereof that will be apparent to those skilled in the art in light of the teachings set forth in B. Mathew et al., *Novel Pyridopyrazine and pyrimidothiazine derivatives as FtsZ inhibitors*, Bioorganic & Med. Chem. 19, 7120-7128 (2011) and E. White et al., Inhibitors of FTSZ and Uses Thereof, U.S. Pat. No. 7,718, 651, the disclosures of which are incorporated by reference herein in their entirety.

The active agents described herein can be used alone or in combination with other compounds that enhance the activity of oligonucleotides, examples of which include but are not limited to the intracellular trafficking inhibitors and retro compounds described in R. Juliano et al., Small Molecules that Enhance the Activity of Oligonucleotides, PCT Application WO 2013/123217 (22 Aug. 2013).

3. OLIGONUCLEOTIDE COMPOUNDS

Any suitable oligonucleotide may be employed, including but not limited to those described in U.S. Pat. No. 7,674,778, the disclosure of which is incorporated by reference herein in its entirety.

The oligonucleotide may include chemical modifications. Specific oligonucleotide chemical modifications are described below. It is not necessary for all positions in a given compound to be uniformly modified, and in fact more than one of the following modifications may be incorporated in a single siRNA compound or even in a single nucleotide thereof. The oligonucleotide may optionally be conjugated to a ligand by any suitable technique, including but not limited to those described in PCT Applications WO2011/126937 to Juliano et al. and WO2009/045536 to Juliano et al.

Some modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalklyphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included. Representative United States patents that teach the preparation of the above phosphorus atom-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, each of which is herein incorporated by reference. Preferred modified internucleoside linkages or backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other oligonucleotide mimetics, both the sugar and the internucleoside linkage, i.e., the backbone, of the nucleoside units are replaced with novel groups. The nucleobase units are maintained for hybridization with an appropriate nucleic acid target compound. One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide-containing backbone, in particular an aminoethylglycine backbone. The nucleobases are retained and are bound directly or indirectly to atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497.

The active compounds disclosed herein can, as noted above, be prepared in the form of their salts, including pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

4. COMPOSITIONS

The invention pertains to uses of the above-described active agents (including both active compounds and oligonucleotides) for methods and treatments as described below. Accordingly, the modulators of the present invention can be incorporated into pharmaceutical compositions suitable for administration. See, e.g., U.S. Pat. No. 7,459,547. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

5. METHODS OF USE

As noted above, the present invention provides a method of introducing an oligonucleotide of interest into a cell, comprising (a) contacting an oligonucleotide compound as described above to the cell in an amount effective to introduce said oligonucleotide into said cell, (b) concurrently with (that is, before, after, or simultaneously with) contacting an active agent to the cell in an amount effective to enhance the activity of said oligonucleotide in said cell. The method may be carried out in vitro or in vivo with any type of cell, particularly animal cells. Animal cells may be mammalian cells, such as human, monkey, cat, dog, rat, mouse, or rabbit cells. The methods may be utilized for any purpose in which it is desired to introduce an oligonucleotide into a cell, including but not limited to those olgioncucleotides (including polynucleotides and RNAi agents) for those purposes described in U.S. Pat. Nos. 7,682,626; 7,674,778; 7,473,419; 7,459,547; and 7,015,040, the disclosures of which are incorporated by reference herein in their entirety.

In some embodiments, the oligonucleotides are splice switching oligonucleotides (SSOs). Examples of suitable SSOs include, but are not limited to, those described in: Kole R, Krainer A R, Altman S., *RNA therapeutics: beyond RNA interference and antisense oligonucleotides*, Nat Rev Drug Discov. 11(2):125-40 (Jan. 20, 2012); S. Cirak et al., *Exon skipping and dystrophin restoration in patients with Duchenne muscular dystrophy after systemic phosphorodiamidate morpholino oligomer treatment: an open-label, phase 2, dose-escalation study*, Lancet 378(9791):595-605 (Aug. 13, 2011); and N M Goemans et al., *Systemic administration of PRO051 in Duchenne's muscular dystrophy* N Engl J Med, 364, 1513-1522 (2011).

In particular embodiments, the oligonucleotide is eteplirsen or drisapersen, administered to the subject for the treatment of duchenne muscular dystrophy. See, e.g., J. Mendell et al., *Ann. Neurol.* 74, 637-647 (2013; K. Flanigan et al., *Neuromuscular Disorders* 24, 16-24 (2014).

In some embodiments, the invention may be used to deliver the oligonucleotides for silencing (in whole or part) the genes described in U.S. Pat. No. 7,674,778, the disclosure of which is incorporated by reference herein in its entirety.

In some embodiments, the invention relates to a method of treating a subject at risk for or afflicted with unwanted cell proliferation, e.g., malignant or nonmalignant cell proliferation. The method comprises providing a ligand-conjugated oligonucleotide agent, wherein the oligonucleotide is homologous to and can silence, e.g., by cleavage, a gene which promotes unwanted cell proliferation; and administering a therapeutically effective dose of the ligand-conjugated oligonucleotide agent to a subject, preferably a human subject.

In an embodiment the gene is a growth factor or growth factor receptor gene, a kinase, e.g., a protein tyrosine, serine or threonine kinase gene, an adaptor protein gene, a gene encoding a G protein superfamily molecule, or a gene encoding a transcription factor.

In an embodiment the oligonucleotide agent silences the PDGF beta gene, and thus can be used to treat a subject having or at risk for a disorder characterized by unwanted PDGF beta expression, e.g., testicular and lung cancers.

In an embodiment the oligonucleotide agent silences the Erb-B gene, and thus can be used to treat a subject having or at risk for a disorder characterized by unwanted Erb-B expression, e.g., breast cancer.

In an embodiment the oligonucleotide agent silences the Src gene, and thus can be used to treat a subject having or at risk for a disorder characterized by unwanted Src expression, e.g., colon cancers.

In an embodiment the oligonucleotide agent silences the CRK gene, and thus can be used to treat a subject having or at risk for a disorder characterized by unwanted CRK expression, e.g., colon and lung cancers.

In an embodiment the oligonucleotide agent silences the GRB2 gene, and thus can be used to treat a subject having or at risk for a disorder characterized by unwanted GRB2 expression, e.g., squamous cell carcinoma.

In an embodiment the oligonucleotide agent silences the RAS gene, and thus can be used to treat a subject having or at risk for a disorder characterized by unwanted RAS expression, e.g., pancreatic, colon and lung cancers, and chronic leukemia.

In an embodiment the oligonucleotide agent silences the MEKK gene, and thus can be used to treat a subject having or at risk for a disorder characterized by unwanted MEKK expression, e.g., squamous cell carcinoma, melanoma or leukemia.

In an embodiment the oligonucleotide agent silences the JNK gene, and thus can be used to treat a subject having or at risk for a disorder characterized by unwanted JNK expression; e.g., pancreatic or breast cancers.

In an embodiment the oligonucleotide agent silences the RAF gene, and thus can be used to treat a subject having or at risk for a disorder characterized by unwanted RAF expression, e.g., lung cancer or leukemia.

In an embodiment the oligonucleotide agent silences the Erk1/2 gene, and thus can be used to treat a subject having or at risk for a disorder characterized by unwanted Erk1/2 expression, e.g., lung cancer.

In an embodiment the oligonucleotide agent silences the PCNA(p21) gene, and thus can be used to treat a subject having or at risk for a disorder characterized by unwanted PCNA expression, e.g., lung cancer.

In an embodiment the oligonucleotide agent silences the MYB gene, and thus can be used to treat a subject having or at risk for a disorder characterized by unwanted MYB expression, e.g., colon cancer or chronic myelogenous leukemia.

In an embodiment the oligonucleotide agent silences the c-MYC gene, and thus can be used to treat a subject having or at risk for a disorder characterized by unwanted c-MYC expression, e.g., Burkitt's lymphoma or neuroblastoma.

In an embodiment the oligonucleotide agent silences the JUN gene, and thus can be used to treat a subject having or at risk for a disorder characterized by unwanted JUN expression, e.g., ovarian, prostate or breast cancers.

In an embodiment the oligonucleotide agent silences the FOS gene, and thus can be used to treat a subject having or at risk for a disorder characterized by unwanted FOS expression, e.g., skin or prostate cancers.

In an embodiment the oligonucleotide agent silences the BCL-2 gene, and thus can be used to treat a subject having or at risk for a disorder characterized by unwanted BCL-2 expression, e.g., lung or prostate cancers or Non-Hodgkin lymphoma.

In an embodiment the oligonucleotide agent silences the Cyclin D gene, and thus can be used to treat a subject having or at risk for a disorder characterized by unwanted Cyclin D expression, e.g., esophageal and colon cancers.

In an embodiment the oligonucleotide agent silences the VEGF gene, and thus can be used to treat a subject having or at risk for a disorder characterized by unwanted VEGF expression, e.g., esophageal and colon cancers.

In an embodiment the oligonucleotide agent silences the EGFR gene, and thus can be used to treat a subject having or at risk for a disorder characterized by unwanted EGFR expression, e.g., breast cancer.

In an embodiment the oligonucleotide agent silences the Cyclin A gene, and thus can be used to treat a subject having or at risk for a disorder characterized by unwanted Cyclin A expression, e.g., lung and cervical cancers.

In an embodiment the oligonucleotide agent silences the Cyclin E gene, and thus can be used to treat a subject having or at risk for a disorder characterized by unwanted Cyclin E expression, e.g., lung and breast cancers.

In an embodiment the oligonucleotide agent silences the WNT-1 gene, and thus can be used to treat a subject having or at risk for a disorder characterized by unwanted WNT-1 expression, e.g., basal cell carcinoma.

In an embodiment the oligonucleotide agent silences the beta-catenin gene, and thus can be used to treat a subject having or at risk for a disorder characterized by unwanted beta-catenin expression, e.g., adenocarcinoma or hepatocellular carcinoma.

In an embodiment the oligonucleotide agent silences the c-MET gene, and thus can be used to treat a subject having or at risk for a disorder characterized by unwanted c-MET expression, e.g., hepatocellular carcinoma.

In an embodiment the oligonucleotide agent silences the PKC gene, and thus can be used to treat a subject having or at risk for a disorder characterized by unwanted PKC expression, e.g., breast cancer.

In an embodiment the oligonucleotide agent silences the NFKB gene, and thus can be used to treat a subject having or at risk for a disorder characterized by unwanted NFKB expression, e.g., breast cancer.

In an embodiment the oligonucleotide agent silences the STAT3 gene, and thus can be used to treat a subject having or at risk for a disorder characterized by unwanted STAT3 expression, e.g., prostate cancer.

In an embodiment the oligonucleotide agent silences the survivin gene, and thus can be used to treat a subject having or at risk for a disorder characterized by unwanted survivin expression, e.g., cervical or pancreatic cancers.

In an embodiment the oligonucleotide agent silences the Her2/Neu gene, and thus can be used to treat a subject having or at risk for a disorder characterized by unwanted Her2/Neu expression, e.g., breast cancer.

In an embodiment the oligonucleotide agent silences the topoisomerase I gene, and thus can be used to treat a subject having or at risk for a disorder characterized by unwanted topoisomerase I expression, e.g., ovarian and colon cancers.

In an embodiment the oligonucleotide agent silences the topoisomerase II alpha gene, and thus can be used to treat a subject having or at risk for a disorder characterized by unwanted topoisomerase II expression, e.g., breast and colon cancers.

In an embodiment the oligonucleotide agent silences mutations in the p73 gene, and thus can be used to treat a subject having or at risk for a disorder characterized by unwanted p73 expression, e.g., colorectal adenocarcinoma.

In an embodiment the oligonucleotide agent silences mutations in the p21(WAF1/CIP1) gene, and thus can be used to treat a subject having or at risk for a disorder characterized by unwanted p21(WAF1/CIP1) expression, e.g., liver cancer.

In an embodiment the oligonucleotide agent silences mutations in the p27(KIP1) gene, and thus can be used to treat a subject having or at risk for a disorder characterized by unwanted p27(KIP1) expression, e.g., liver cancer.

In an embodiment the oligonucleotide agent silences mutations in the PPM1D gene, and thus can be used to treat a subject having or at risk for a disorder characterized by unwanted PPM1D expression, e.g., breast cancer.

In an embodiment the oligonucleotide agent silences mutations in the RAS gene, and thus can be used to treat a subject having or at risk for a disorder characterized by unwanted RAS expression, e.g., breast cancer.

In an embodiment the oligonucleotide agent silences mutations in the caveolin I gene, and thus can be used to treat a subject having or at risk for a disorder characterized by unwanted caveolin I expression, e.g., esophageal squamous cell carcinoma.

In an embodiment the oligonucleotide agent silences mutations in the MIB I gene, and thus can be used to treat a subject having or at risk for a disorder characterized by unwanted MIB I expression, e.g., male breast carcinoma (MBC).

In an embodiment the oligonucleotide agent silences mutations in the MTAI gene, and thus can be used to treat a subject having or at risk for a disorder characterized by unwanted MTAI expression, e.g., ovarian carcinoma.

In an embodiment the oligonucleotide agent silences mutations in the M68 gene, and thus can be used to treat a subject having or at risk for a disorder characterized by unwanted M68 expression, e.g., human adenocarcinomas of the esophagus, stomach, colon, and rectum.

In preferred embodiments the oligonucleotide agent silences mutations in tumor suppressor genes, and thus can be used as a method to promote apoptotic activity in combination with chemotherapeutics.

In an embodiment the oligonucleotide agent silences mutations in the p53 tumor suppressor-gene, and thus can be used to treat a subject having or at risk for a disorder characterized by unwanted p53 expression, e.g., gall bladder, pancreatic and lung cancers.

In an embodiment the oligonucleotide agent silences mutations in the p53 family member DN-p63, and thus can be used to treat a subject having or at risk for a disorder characterized by unwanted DN-p63 expression, e.g., squamous cell carcinoma.

In an embodiment the oligonucleotide agent silences mutations in the pRb tumor suppressor gene, and thus can be used to treat a subject having or at risk for a disorder characterized by unwanted pRb expression, e.g., oral squamous cell carcinoma.

In an embodiment the oligonucleotide agent silences mutations in the APC1 tumor suppressor gene, and thus can be used to treat a subject having or at risk for a disorder characterized by unwanted APC1 expression, e.g., colon cancer.

In an embodiment the oligonucleotide agent silences mutations in the BRCA1 tumor suppressor gene, and thus can be used to treat a subject having or at risk for a disorder characterized by unwanted BRCA1 expression, e.g., breast cancer.

In an embodiment the oligonucleotide agent silences mutations in the PTEN tumor suppressor gene, and thus can be used to treat a subject having or at risk for a disorder characterized by unwanted PTEN expression, e.g., hamartomas, gliomas, and prostate and endometrial cancers.

In an embodiment the oligonucleotide agent silences MLL fusion genes, e.g., MLL-AF9, and thus can be used to treat a subject having or at risk for a disorder characterized by unwanted MLL fusion gene expression, e.g., acute leukemias.

In an embodiment the oligonucleotide agent silences the BCR/ABL fusion gene, and thus can be used to treat a subject having or at risk for a disorder characterized by unwanted BCR/ABL fusion gene expression, e.g., acute and chronic leukemias.

In an embodiment the oligonucleotide agent silences the TEL/AML1 fusion gene, and thus can be used to treat a subject having or at risk for a disorder characterized by unwanted TEL/AML1 fusion gene expression, e.g., childhood acute leukemia.

In an embodiment the oligonucleotide agent silences the EWS/FLI1 fusion gene, and thus can be used to treat a subject having or at risk for a disorder characterized by unwanted EWS/FLI1 fusion gene expression, e.g., Ewing Sarcoma.

In an embodiment the oligonucleotide agent silences the TLS/FUS1 fusion gene, and thus can be used to treat a subject having or at risk for a disorder characterized by unwanted TLS/FUS1 fusion gene expression, e.g., Myxoid liposarcoma.

In an embodiment the oligonucleotide agent silences the PAX3/FKHR fusion gene, and thus can be used to treat a subject having or at risk for a disorder characterized by unwanted PAX3/FKHR fusion gene expression, e.g., Myxoid liposarcoma.

In an embodiment the oligonucleotide agent silences the AML1/ETO fusion gene, and thus can be used to treat a subject having or at risk for a disorder characterized by unwanted AML1/ETO fusion gene expression, e.g., acute leukemia.

Another aspect of the invention relates to a method of treating a subject, e.g., a human, at risk for or afflicted with a disease or disorder that may benefit by angiogenesis inhibition e.g., cancer. The method comprises providing a ligand-conjugated oligonucleotide agent, wherein said oligonucleotide agent is homologous to and can silence, e.g., by cleavage, a gene which mediates angiogenesis; and administering a therapeutically effective dosage of said ligand-conjugated oligonucleotide agent to a subject, preferably a human.

In an embodiment the oligonucleotide agent silences the alpha v-integrin gene, and thus can be used to treat a subject having or at risk for a disorder characterized by unwanted alpha V integrin, e.g., brain tumors or tumors of epithelial origin.

In an embodiment the oligonucleotide agent silences the Fit-1 receptor gene, and thus can be used to treat a subject having or at risk for a disorder characterized by unwanted Flt-1 receptors, eg. Cancer and rheumatoid arthritis.

In an embodiment the oligonucleotide agent silences the tubulin gene, and thus can be used to treat a subject having or at risk for a disorder characterized by unwanted tubulin, eg. Cancer and retinal neovascularization.

Another aspect of the invention relates to a method of treating a subject infected with a virus or at risk for or afflicted with a disorder or disease associated with a viral infection.

The method comprises providing a ligand-conjugated oligonucleotide agent, wherein said oligonucleotide agent is homologous to and can silence, e.g., by cleavage, a viral gene of a cellular gene which mediates viral function, e.g., entry or growth; and administering a therapeutically effective dose of said ligand-conjugated oligonucleotide agent to a subject, preferably a human subject.

Thus, the invention provides for a method of treating patients infected by the Human Papilloma Virus (HPV) or at risk for or afflicted with a disorder mediated by HPV, e.g, cervical cancer. HPV is linked to 95% of cervical carcinomas and thus an antiviral therapy is an attractive method to treat these cancers and other symptoms of viral infection.

In an embodiment, the expression of a HPV gene is reduced. In an embodiment, the HPV gene is one of the group of E2, E6, or E7.

In an embodiment the expression of a human gene that is required for HPV replication is reduced.

The invention also includes a method of treating patients infected by the Human Immunodeficiency Virus (HIV) or at risk for or afflicted with a disorder mediated by HIV, e.g., Acquired Immune Deficiency Syndrome (AIDS). In an embodiment, the expression of a HIV gene is reduced. In an embodiment, the HIV gene is CCR5, Gag, or Rev. In an embodiment the expression of a human gene that is required for HIV replication is reduced. In an embodiment, the gene is CD4 or Tsg101.

The invention also includes a method for treating patients infected by the Hepatitis B Virus (HBV) or at risk for or afflicted with a disorder mediated by HBV, e.g., cirrhosis and heptocellular carcinoma. In an embodiment, the expression of a HBV gene is reduced. In an embodiment, the targeted HBV gene encodes one of the group of the tail region of the HBV core protein, the pre-cregious (pre-c) region, or the cregious (c) region. In an embodiment, a targeted HBV-RNA sequence is comprised of the poly(A) tail.

In preferred embodiment the expression of a human gene that is required for HBV replication is reduced.

The invention also provides for a method of treating patients infected by the Hepatitis A Virus (HAV), or at risk for or afflicted with a disorder mediated by HAV. In an embodiment the expression of a human gene that is required for HAV replication is reduced.

The present invention provides for a method of treating patients infected by the Hepatitis C Virus (HCV), or at risk for or afflicted with a disorder mediated by HCV, e.g., cirrhosis. In an embodiment, the expression of a HCV gene is reduced. In an embodiment the expression of a human gene that is required for HCV replication is reduced.

The present invention also provides for a method of treating patients infected by the any of the group of Hepatitis Viral strains comprising hepatitis D, E, F, G, or H, or patients at risk for or afflicted with a disorder mediated by any of these strains of hepatitis. In an embodiment, the expression of a Hepatitis, D, E, F, G, or H gene is reduced. In an embodiment the expression of a human gene that is required for hepatitis D, E, F, G or H replication is reduced.

Methods of the invention also provide for treating patients infected by the Respiratory Syncytial Virus (RSV) or at risk for or afflicted with a disorder mediated by RSV, e.g, lower respiratory tract infection in infants and childhood asthma, pneumonia and other complications, e.g., in the elderly. In an embodiment, the expression of a RSV gene is reduced. In an embodiment, the targeted HBV gene encodes one of the group of genes N, L, or P. In an embodiment the expression of a human gene that is required for RSV replication is reduced.

Methods of the invention provide for treating patients infected by the Herpes Simplex Virus (HSV) or at risk for or afflicted with a disorder mediated by HSV, e.g, genital herpes and cold sores as well as life-threatening or sight-impairing disease mainly in immunocompromised patients. In an embodiment, the expression of a HSV gene is reduced. In an embodiment, the targeted HSV gene encodes DNA polymerase or the helicase-primase. In an embodiment the expression of a human gene that is required for HSV replication is reduced.

The invention also provides a method for treating patients infected by the herpes Cytomegalovirus (CMV) or at risk for or afflicted with a disorder mediated by CMV, e.g., congenital virus infections and morbidity in immunocompromised patients. In an embodiment, the expression of a CMV gene is reduced. In an embodiment the expression of a human gene that is required for CMV replication is reduced.

Methods of the invention also provide for a method of treating patients infected by the herpes Epstein Barr Virus (EBV) or at risk for or afflicted with a disorder mediated by EBV, e.g., NK/T-cell lymphoma, non-Hodgkin lymphoma, and Hodgkin disease. In an embodiment, the expression of a EBV gene is reduced. In an embodiment the expression of a human gene that is required for EBV replication is reduced.

Methods of the invention also provide for treating patients infected by Kaposi's Sarcoma-associated Herpes Virus (KSHV), also called human herpesvirus 8, or patients at risk for or afflicted with a disorder mediated by KSHV, e.g., Kaposi's sarcoma, multicentric Castleman's disease and AIDS-associated primary effusion lymphoma. In an embodiment, the expression of a KSHV gene is reduced. In an embodiment the expression of a human gene that is required for KSHV replication is reduced.

The invention also includes a method for treating patients infected by the JC Virus (JCV) or a disease or disorder associated with this virus, e.g., progressive multifocal leukoencephalopathy (PML). In an embodiment, the expression of a JCV gene is reduced. In preferred embodiment the expression of a human gene that is required for JCV replication is reduced.

Methods of the invention also provide for treating patients infected by the myxovirus or at risk for or afflicted with a disorder mediated by myxovirus, e.g., influenza. In an embodiment, the expression of a myxovirus gene is reduced. In an embodiment the expression of a human gene that is required for myxovirus replication is reduced.

Methods of the invention also provide for treating patients infected by the rhinovirus or at risk for of afflicted with a disorder mediated by rhinovirus, e.g., the common cold. In an embodiment, the expression of a rhinovirus gene is reduced. In preferred embodiment the expression of a human gene that is required for rhinovirus replication is reduced.

Methods of the invention also provide for treating patients infected by the coronavirus or at risk for of afflicted with a disorder mediated by coronavirus, e.g., the common cold. In an embodiment, the expression of a coronavirus gene is reduced. In preferred embodiment the expression of a human gene that is required for coronavirus replication is reduced.

Methods of the invention also provide for treating patients infected by the flavivirus West Nile or at risk for or afflicted with a disorder mediated by West Nile Virus. In an embodiment, the expression of a West Nile Virus gene is reduced. In an embodiment, the West Nile Virus gene is one of the group comprising E, NS3, or NS5. In an embodiment the expression of a human gene that is required for West Nile Virus replication is reduced.

Methods of the invention also provide for treating patients infected by the St. Louis Encephalitis flavivirus, or at risk for or afflicted with a disease or disorder associated with this virus, e.g., viral haemorrhagic fever or neurological disease. In an embodiment, the expression of a St. Louis Encephalitis gene is reduced. In an embodiment the expression of a human gene that is required for St. Louis Encephalitis virus replication is reduced.

Methods of the invention also provide for treating patients infected by the Tick-borne encephalitis flavivirus, or at risk for or afflicted with a disorder mediated by Tick-borne encephalitis virus, e.g., viral haemorrhagic fever and neurological disease. In an embodiment, the expression of a Tick-borne encephalitis virus gene is reduced. In an embodiment the expression of a human gene that is required for Tick-borne encephalitis virus replication is reduced.

Methods of the invention also provide for methods of treating patients infected by the Murray Valley encephalitis flavivirus, which commonly results in viral haemorrhagic fever and neurological disease. In an embodiment, the expression of a Murray Valley encephalitis virus gene is reduced. In an embodiment the expression of a human gene that is required for Murray Valley encephalitis virus replication is reduced.

The invention also includes methods for treating patients infected by the dengue flavivirus, or a disease or disorder associated with this virus, e.g., dengue haemorrhagic fever. In an embodiment, the expression of a dengue virus gene is reduced. In an embodiment the expression of a human gene that is required for dengue virus replication is reduced.

Methods of the invention also provide for treating patients infected by the Simian Virus 40 (SV40) or at risk for or afflicted with a disorder mediated by SV40, e.g., tumorigenesis. In an embodiment, the expression of a SV40 gene is reduced. In an embodiment the expression of a human gene that is required for SV40 replication is reduced.

The invention also includes methods for treating patients infected by the Human T Cell Lymphotropic Virus (HTLV), or a disease or disorder associated with this virus, e.g., leukemia and myelopathy. In an embodiment, the expression of a HTLV gene is reduced. In an embodiment the HTLV1 gene is the Tax transcriptional activator. In an embodiment the expression of a human gene that is required for HTLV replication is reduced.

Methods of the invention also provide for treating patients infected by the Moloney-Murine Leukemia Virus (Mo-MuLV) or at risk for or afflicted with a disorder mediated by Mo-MuLV, e.g., T-cell leukemia. In an embodiment, the expression of a Mo-MuLV gene is reduced. In an embodiment the expression of a human gene that is required for Mo-MuLV replication is reduced.

Methods of the invention also provide for treating patients infected by the encephalomyocarditis virus (EMCV) or at risk for or afflicted with a disorder mediated by EMCV, e.g. myocarditis. EMCV leads to myocarditis in mice and pigs and is capable of infecting human myocardial cells. This virus is therefore a concern for patients undergoing xenotransplantation. In an embodiment, the expression of a EMCV gene is reduced. In an embodiment the expression of a human gene that is required for EMCV replication is reduced.

The invention also includes a method for treating patients infected by the measles virus (MV) or at risk for or afflicted with a disorder mediated by MV, e.g., measles. In an embodiment, the expression of a MV gene is reduced. In an embodiment the expression of a human gene that is required for MV replication is reduced.

The invention also includes a method for treating patients infected by the Vericella zoster virus (VZV) or at risk for or afflicted with a disorder mediated by VZV, e.g. chicken pox or shingles (also called zoster). In an embodiment, the expression of a VZV gene is reduced. In an embodiment the expression of a human gene that is required for VZV replication is reduced.

The invention also includes a method for treating patients infected by an adenovirus or at risk for or afflicted with a disorder mediated by an adenovirus, e.g. respiratory tract infection. In an embodiment, the expression of an adenovirus gene is reduced. In an embodiment the expression of a human gene that is required for adenovirus replication is reduced.

The invention includes a method for treating patients infected by a yellow fever virus (YFV) or at risk for or afflicted with a disorder mediated by a YFV, e.g. respiratory tract infection. In an embodiment, the expression of a YFV gene is reduced. In an embodiment, the preferred gene is one of a group that includes the E, NS2A, or NS3 genes. In an embodiment the expression of a human gene that is required for YFV replication is reduced.

Methods of the invention also provide for treating patients infected by the poliovirus or at risk for or afflicted with a disorder mediated by poliovirus, e.g., polio. In an embodiment, the expression of a poliovirus gene is reduced. In an embodiment the expression of a human gene that is required for poliovirus replication is reduced.

Methods of the invention also provide for treating patients infected by a poxvirus or at risk for or afflicted with a disorder mediated by a poxvirus, e.g., smallpox. In an embodiment, the expression of a poxvirus gene is reduced. In an embodiment the expression of a human gene that is required for poxvirus replication is reduced.

In another, aspect the invention features methods of treating a subject infected with a pathogen, e.g., a bacterial, amoebic, parasitic, or fungal pathogen. The method comprises providing a ligand-conjugated oligonucleotide agent, wherein said oligonucleotide is homologous to and can silence, e.g., by cleavage of a pathogen gene; and administering a therapeutically effective dose of said ligand-conjugated oligonucleotide agent to a subject, preferably a human subject.

The target gene can be one involved in growth, cell wall synthesis, protein synthesis, transcription, energy metabolism, e.g., the Krebs cycle, or toxin production. Thus, the present invention provides for a method of treating patients infected by a *plasmodium* that causes malaria. In an embodiment, the expression of a *plasmodium* gene is reduced. In an embodiment, the gene is apical membrane antigen 1 (AMA1). In an embodiment the expression of a human gene that is required for *plasmodium* replication is reduced.

The invention also includes methods for treating patients infected by the *Mycobacterium ulcerans*, or a disease or disorder associated with this pathogen, e.g. Buruli ulcers. In an embodiment, the expression of a *Mycobacterium ulcerans* gene is reduced. In an embodiment the expression of a human gene that is required for *Mycobacterium ulcerans* replication is reduced.

The invention also includes methods for treating patients infected by the *Mycobacterium tuberculosis*, or a disease or disorder associated with this pathogen, e.g. tuberculosis. In an embodiment, the expression of a *Mycobacterium tuberculosis* gene is reduced. In an embodiment the expression of a human gene that is required for *Mycobacterium tuberculosis* replication is reduced.

The invention also includes methods for treating patients infected by the *Mycobacterium leprae*, or a disease or disorder associated with this pathogen, e.g. leprosy. In an embodiment, the expression of a *Mycobacterium leprae* gene is reduced. In an embodiment the expression of a human gene that is required for *Mycobacterium leprae* replication is reduced.

The invention also includes methods for treating patients infected by the bacteria *Staphylococcus aureus*, or a disease or disorder associated with this pathogen, e.g. infections of the skin and muscous membranes. In an embodiment, the expression of a *Staphylococcus aureus* gene is reduced. In an embodiment the expression of a human gene that is required for *Staphylococcus aureus* replication is reduced.

The invention also includes methods for treating patients infected by the bacteria *Streptococcus pneumoniae*, or a disease or disorder associated with this pathogen, e.g. pneumonia or childhood lower respiratory tract infection. In an embodiment, the expression of a *Streptococcus pneumoniae* gene is reduced. In an embodiment the expression of a human gene that is required for *Streptococcus pneumoniae* replication is reduced.

The invention also includes methods for treating patients infected by the bacteria *Streptococcus pyogenes*, or a disease or disorder associated with this pathogen, e.g. Strep throat or Scarlet fever. In an embodiment, the expression of a *Streptococcus pyogenes* gene is reduced. In an embodiment the expression of a human gene that is required for *Streptococcus pyogenes* replication is reduced.

The invention also includes methods for treating patients infected by the bacteria *Chlamydia pneumoniae*, or a disease or disorder associated with this pathogen, e.g. pneumonia or childhood lower respiratory tract infection. In an embodiment, the expression of a *Chlamydia pneumoniae* gene is reduced. In an embodiment the expression of a human gene that is required for *Chlamydia pneumoniae* replication is reduced.

The invention also includes methods for treating patients infected by the bacteria *Mycoplasma pneumoniae*, or a disease or disorder associated with this pathogen, e.g. pneumonia or childhood lower respiratory tract infection. In an embodiment, the expression of a *Mycoplasma pneumoniae* gene is reduced. In an embodiment the expression of a human gene that is required for *Mycoplasma pneumoniae* replication is reduced.

Another aspect of the invention relates to a method of treating a subject, e.g., a human, at risk for or afflicted with a disease or disorder characterized by an unwanted immune response, e.g., an inflammatory disease or disorder, or an autoimmune disease or disorder. The method comprises providing a ligand-conjugated oligonucleotide agent, wherein said oligonucleotide agent is homologous to and can silence, e.g., by cleavage, a gene which mediates an unwanted immune response; and administering said ligand-conjugated oligonucleotide agent to a subject, preferrably a human subject. In an embodiment the disease or disorder is an ischemia or reperfusion injury, e.g., ischemia or reperfusion injury associated with acute myocardial infarction, unstable angina, cardiopulmonary bypass, surgical intervention e.g., angioplasty, e.g., percutaneous transluminal coronary angioplasty, the response to a transplanted organ or tissue, e.g., transplanted cardiac or vascular tissue; or thrombolysis. In an embodiment the disease or disorder is restenosis, e.g., restenosis associated with surgical intervention e.g., angioplasty, e.g., percutaneous transluminal coronary angioplasty. In a preferred embodiment the disease or disorder is Inflammatory Bowel Disease, e.g., Crohn Disease or Ulcerative Colitis. In a preferred embodiment the disease or disorder is inflammation associated with an infection or injury. In a preferred embodiment the disease or disorder is asthma, lupus, multiple sclerosis, diabetes, e.g., type II diabetes, arthritis, e.g., rheumatoid or psoriatic. In particularly preferred embodiments the oligonucleotide agent silences an integrin or co-ligand thereof, e.g., VLA4, VCAM, ICAM. In particularly preferred embodiments the oligonucleotide agent silences a selectin or co-ligand thereof, e.g., P-selectin, E-selectin (ELAM), I-selectin, P-selectin glycoprotein-1 (PSGL-1). In particularly preferred embodiments the oligonucleotide agent silences a component of the complement system, e.g., C3, C5, C3aR, C5aR, C3 convertase, C5 convertase.

In particularly preferred embodiments the oligonucleotide agent silences a chemokine or receptor thereof, e.g., TNFI, TNFJ, IL-1I, IL-1J, IL-2, IL-2R, IL-4, IL-4R, IL-5, IL-6, IL-8, TNFRI, TNFRII, IgE, SCYA11, CCR3.

In other embodiments the oligonucleotide agent silences GCSF, Gro1, Gro2, Gro3, PF4, MIG, Pro-Platelet Basic Protein (PPBP), MIP-11, MIP-1J, RANTES, MCP-1, MCP-2, MCP-3, CMBKR1, CMBKR2, CMBKR3, CMBKR5, AIF-1, 1-309.

Another aspect of the invention features, a method of treating a subject, e.g., a human, at risk for or afflicted with acute pain or chronic pain. The method comprises providing a ligand-conjugated oligonucleotide agent, wherein said ligand is an aromatic group and said oligonucleotide is homologous to and can silence, e.g., by cleavage, a gene which mediates the processing of pain; and administering a therapeutically effective dose of said ligand-conjugated oligonucleotide agent to a subject, preferably a human subject. In particularly preferred embodiments the oligonucleotide agent silences a component of an ion channel. In particularly preferred embodiments the oligonucleotide agent silences a neurotransmitter receptor or ligand.

Another aspect of the invention relates to a method of treating a subject, e.g., a human, at risk for or afflicted with a neurological disease or disorder. The method comprises providing a ligand-conjugated oligonucleotide agent, wherein said ligand is an aromtic group and said oligonucleotide is homologous to and can silence, e.g., by cleavage, a gene which mediates a neurological disease or disorder; and administering a therapeutically effective dose of said ligand-conjugated oligonucleotide agent the to a subject, preferrably a human. In a preferred embodiment the disease or disorder is Alzheimer Disease or Parkinson Disease. In particularly preferred embodiments the oligonucleotide agent silences an amyloid-family gene, e.g., APP; a presenilin gene, e.g., PSEN1 and PSEN2, or I-synuclein. In an embodiment the disease or disorder is a neurodegenerative trinucleotide repeat disorder, e.g., Huntington disease, dentatorubral pallidoluysian atrophy or a spinocerebellar ataxia, e.g., SCA1, SCA2, SCA3 (Machado-Joseph disease), SCA7 or SCA8.

In particularly preferred embodiments the oligonucleotide agent silences HD, DRPLA, SCA1, SCA2, MJD1, CACNL1A4, SCA7, SCA8.

The loss of heterozygosity (LOH) can result in hemizygosity for sequence, e.g., genes, in the area of LOH. This can result in a significant genetic difference between normal and disease-state cells, e.g., cancer cells, and provides a useful difference between normal and disease-state cells, e.g., cancer cells. This difference can arise because a gene or other sequence is heterozygous in euploid cells but is hemizygous in cells having LOH. The regions of LOH will often include a gene, the loss of which promotes unwanted proliferation, e.g., a tumor suppressor gene, and other sequences including, e.g., other genes, in some cases a gene which is essential for normal function, e.g., growth. Methods of the invention rely, in part, on the specific cleavage or silencing of one allele of an essential gene with a ligand-conjugated oligonucleotide agent of the invention. The oligonucleotide agent is selected such that it targets the single allele of the essential gene found in the cells having LOH but does not silence the other allele, which is present in cells which do not show LOH. In essence, it discriminates between the two alleles, preferentially silencing the selected allele. In essence polymorphisms, e.g., SNPs of essential genes that are affected by LOH, are used as a target for a disorder characterized by cells having LOH, e.g., cancer cells having LOH. E.g., one of ordinary skill in the art can identify essential genes which are in proximity to tumor suppressor genes, and which are within a LOH region which includes the tumor suppressor gene. The gene encoding the large subunit of human RNA polymerase II, POLR2A, a gene located in close proximity to the tumor suppressor gene p53, is such a gene. It frequently occurs within a region of LOH in cancer cells. Other genes that occur within LOH regions and are lost in many cancer cell types include the group comprising replication protein A 70-kDa subunit, replication protein A 32-kD, ribonucleotide reductase, thymidilate synthase, TATA associated factor 2H, ribosomal protein S14, eukaryotic initiation factor 5A, alanyl tRNA synthetase, cysteinyl tRNA synthetase, NaK ATPase, alpha-1 subunit, and transferrin receptor.

Accordingly, another aspect of the invention relates to a method of treating a disorder characterized by LOH, e.g., cancer. The method comprises optionally, determining the genotype of the allele of a gene in the region of LOH and preferably determining the genotype of both alleles of the gene in a normal cell; providing a ligand-conjugated oligonucleotide agent which preferentially cleaves or silences the allele found in the LOH cells; and administering a therapeutically effective dose of said ligand-conjugated oligonucleotide agent to the subject, preferably a human.

The invention also includes a ligand-conjugated oligonucleotide agent disclosed herein, e.g, an oligonucleotide agent which can preferentially silence, e.g., cleave, one allele of a polymorphic gene.

In another aspect, the invention provides a method of cleaving or silencing more than one gene with a ligand-conjugated oligonucleotide agent. In these embodiments the oligonucleotide agent is selected so that it has sufficient homology to a sequence found in more than one gene. For example, the sequence AAGCTGGCCCTGGACATGGAGAT (SEQ ID NO:1) is conserved between mouse lamin B1, lamin B2, keratin complex 2-gene 1 and lamin A/C. Thus an oligonucleotide agent targeted to this sequence would effectively silence the entire collection of genes.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

The present invention is explained in greater detail in the following non-limiting Examples.

EXPERIMENTAL

A high throughput screen of multiple small molecule libraries yielded several hits that markedly potentiated the actions of splice switching oligonucleotides in cell culture. These compounds also enhanced the effects of antisense and siRNA oligonucleotides. The hit compounds preferentially caused release of fluorescent oligonucleotides from late endosomes rather than other intracellular compartments. Studies in a transgenic mouse model indicated that these compounds could enhance the in vivo effects of a splice-switching oligonucleotide without causing significant toxicity.

Materials and Methods

Oligonucleotides, Cell Lines and Other Reagents.

The 2'-O-Me phosphorothioate splice switching oligonucleotide SSO0623 [5'-GTTATTCTTTAGAATGGTGC-3'] (SEQ ID NO:2), its 5 base mismatch control [5'-GTAAT-TATTTATAATCGTCC-3'] (SEQ ID NO:3) and 3' carboxytetramethylrhodamine (TAMRA) conjugated versions were synthesized as described (Alam, M. R. et al., Nucleic Acids Res, 36, 2764-2776 (2008)). A 200 mg batch of SS0623 for in vivo studies was prepared by Avecia (Milford, Mass.). A 2'-O-Me gapmer phosphorothioate anti-MDR1 antisense oligonucleotide (5'-CCATCccgac-ctcgcGCTCC-3') (SEQ ID NO:4) [2'-O-Me modifications in capitals] and its scrambled control were obtained from Integrated DNA Technologies (Coralville, Iowa). A SSO (5'-TGGTTCTTACCCAGCCGCCG-3') (SEQ ID NO:5) that causes redirection of Bcl-x pre-mRNA splicing from Bcl-xL to -xS has been previously described (Bauman, J. A. et al., Nucleic Acids Res, 38, 8348-8356 (2010)). Cholesterol modified siRNA targeting EGFP (5'-gccacaacgucuauaucau-3') (SEQ ID NO:6) and its mismatch control were obtained from Invitrogen/Life Technologies (Carlsbad, Calif.). RNA isolation and reverse transcriptase-polymerase chain reaction analysis (RT-PCR) for Bcl-x and for EGFP were performed as previously described using the specified primers (Ming, X. et al., Nucleic Acids Res, 41, 3673-3687 (2013)). An Alexa 488-tagged monoclonal antibody to P-glycoprotein (Pgp) was from BD-Pharmingen (San Jose, Calif.). Lipofectamine 2000, LysoTracker Green® lysosomotropic dye, Alexa 488 labeled dextran and baculovirus expression systems (Organelle Lights™) were obtained from Invitrogen/Life Technologies (Carlsbad, Calif.). HeLaEGFP654 is a human cell line containing an enhanced GFP reporter interrupted by an abnormal intron. HeLaLuc705 and the human melanoma line A375Luc705 contain a similarly structured luciferase reporter (Alam, M. R. et al., Nucleic Acids Res, 36, 2764-2776 (2008); Ming, X. et al., Nucleic Acids Res, 41, 3673-3687 (2013)). In each of these cell lines, correct splicing and reporter expression can be restored by delivery of SS0623 to the nucleus. NIH-3T3-MDR is a mouse fibroblast cell line stably transfected with a complementary DNA coding for the human Pgp multi-drug transporter and was obtained from M. Gottesmann (National Cancer Institute).

Compound Libraries.

The UNC compound libraries used in this study as well as our general approaches to high throughput screening have been previously described (Wigle, T. J., et al. Journal of biomolecular screening, 15, 62-71 (2010), Hutti, J. E., et al. PLoS One, 7, e41494, Kireev, D, et al. Journal of medicinal chemistry, 53, 7625-7631 (2010), Peterson, E. J., et al., Assay and drug development technologies, 10, 260-268 (2012)). The Southern Research Library, the source of the three hits studied here, is a 13,392 compound collection made available through a collaboration between UNC and the Southern Research Institute.

High Throughput Screening.

Our high throughput screen (HTS) utilized HeLaLuc705 cells. Delivery of an appropriate SSO to the nucleus corrects splicing and induces luciferase expression thus providing an easily interpreted positive readout (Iam, M. R. et al., Nucleic Acids Res, 36, 2764-2776 (2008), Ming, X., et al., Nucleic Acids Res, 38, 6567-6576 (2010)). Cells were trypsinized, rinsed, and suspended in Opti-MEM at 300,000 cells/ml; SSO623 was added to a final concentration of 100 nM. No lipid or polymer transfection agents were used in these assays. Opti-MEM (15 ul) followed by cell suspension (20 ul) was added to wells of 384 well plates. Cells were allowed to attach and incubate with the SSO for 16 h. During this 16 h period a set of positive control wells received chloroquine to a final concentration of 300 uM while a set of negative control wells received diluent. After the initial incubation the remaining wells received library compounds to a final concentration of 25 uM. Incubation with library compounds was at 37 C for 5 h at which time the cells were harvested and analyzed for luciferase induction. Library compounds that produced an induction of 50% that of the positive controls were considered positive in this assay and were further analyzed. Dose-response curves were developed comparing SSO623 with a mis-matched oligonucleotide. Compounds that fully discriminated active SSO from its mismatched control were considered to be legitimate hits.

SSO, Antisense and siRNA Assays.

Luciferase induction dose-response curves in a 24 well plate format with normalization on cell protein were performed as previously described (Alam, M. R. et al., Nucleic Acids Res, 36, 2764-2776 (2008), Ming, X., et al., Nucleic Acids Res, 38, 6567-6576 (2010)). Splicing modulation of the EGFP654 reporter and of endogenous Bcl-X were monitored by RT-PCR using appropriate primers. Evaluation of hit compound effects on antisense actions involved 'knockdown' of MDR1 pre-mRNA and its protein product in multi-drug resistant mouse 3T3 cells. Cell surface expression of P-glycoprotein was monitored using an Alexa-488 conjugated monoclonal antibody and flow cytometry as previously described (Ming, X. et al., Nucleic Acids Res, 41, 3673-3687 (2013), Fisher, M., et al., Nucleic Acids Res, 35, 1064-1074 (2007)). Evaluation of effects on siRNA utilized a HeLa cell line stably transfected with an EGFP expression cassette. Cholesterol-conjugated siRNAs were used to attain sufficient uptake. Cells were incubated with the siEGFP or control siRNA, rinsed, and then briefly exposed to hit compound. After further incubation expression of EGFP was monitored by flow cytometry. In cases where treatment with Lipofectamine 2000 was used as a positive control, the manufacturer's protocol was followed.

Cytotoxicity.

An Alamar Blue assay was used to measure cytotoxicity Ming, X., et al., Drug metabolism and disposition: the biological fate of chemicals, 37, 424-430 (2009)). Cells were incubated with hit compounds under the same conditions as used for dose-response assays. After removal of the hit compound, cells were further incubated for 24 h-72 h in complete medium and then tested.

Confocal Studies.

Quantitative live cell confocal microscopy (Dunn, K. W., et al., Am J Physiol Cell Physiol, 300, C723-742 (2011)) was performed to examine the subcellular distribution of fluorescent oligonucleotide or of certain markers for endomembrane compartments. Cells (HeLa) were transfected with baculovirus expression vectors for GFP chimeras of marker proteins for several endomembrane compartments. The day following transfection, cells were incubated for 4 h with 300 nM TAMRA conjugated SSO 623 in OptiMEM after which the cells were washed and incubated in DMEM medium with 1% FBS. In some cases hit compounds were added during or after the incubation. Cells were imaged on an Olympus FV1000 MPE laser scanning confocal microscope with environmental chamber to maintain 37 C, 40% humidity and 5% C02. We used 488 nm (GFP) and 559 nm (TAMRA) as laser lines, and images were collected with a 60× oil immersion lens. Quantitation of co-localization of oligonucleotide and marker proteins utilized the Coloc2 plug-in in Image J. In some cases GFP markers for organelles were examined in cells previously fixed in 4% formaldehyde in PBS.

Flow Cytometry.

Measurement of Pgp expression and Lysotracker Green accumulation were performed by flow cytometery using an LSR II cell analyser (Becton-Dickenson, San Jose, Calif., USA) as previously described (Ming, X. et al., Nucleic Acids Res, 41, 3673-3687 (2013)).

In Vivo Effects and Toxicity.

All animal procedures were in accordance with guidelines of the UNC Laboratory Animal Medicine Department and with federal guidelines. The EGFP654 transgenic mouse has been described previously (Sazani, P., et al., Nature biotechnology, 20, 1228-1233 (2002), Roberts, J., et al., Mol Ther, 14, 471-475 (2006)). A reporter gene comprised of the EGFP coding sequence is interrupted by an aberrantly spliced intron. Delivery of an appropriate SSO to the nucleus of tissue cells will correct splicing leading the expression of normal EGFP mRNA and protein. EGFP654 mice were administered 25 mg/kg SS0623 or mis-matched oligonucleotide in PBS by intra-peritoneal injection on two consecutive days. One day later the mice received 7.5 mg/kg UNC10217938A intravenously in a diluent of 5% PEG400, or diluent only. After 24 h the mice were euthanized and cardiac blood and tissues samples collected. Tissues for fluorescence microscopy to visualize EGFP were fixed in cold 1.5% paraformaldehyde in PBS and then processed for cryosectioning (Sazani, P., et al., Nature biotechnology, 20, 1228-1233 (2002)). Tissues for RNA analysis were collected from mice euthanized at 4 h and ere quick frozen on dry ice. All procedures involving live animals were conducted by the UNC Animal Studies Core facility. Blood samples were analyzed by the UNC Animal Clinical Chemistry Core facility.

Results

High Throughput Screening.

Our high throughput screening (HTS) effort utilized a splice switching oligonucleotide (termed SS0623) and our previously described luciferase induction assay (Alam, M. R. et al., Nucleic Acids Res, 36, 2764-2776 (2008), Ming, X., et al., Nucleic Acids Res, 38, 6567-6576 (2010), Ming, X. et al., Nucleic Acids Res, 41, 3673-3687 (2013)) optimized for screening. We screened >100,000 compounds from several libraries using a 384 well format. The Z-values were 0.8 or greater in all cases. The total number of hits was rather low, totaling only 67 or 0.04%. The majority of the hits were confirmed using the primary assay, but many also induced activity with a mismatched oligonucleotide and were designated as false positives since they made the splicesosome less discriminating and thus increased spontaneous splice correction; many of the strongest hits fell into this category. Following stringent secondary assays we identified three distinct series of compounds that met the following criteria: (a) they strongly increased luciferase induction by SSO623 but not a mismatched oligonucleotide; (b) they were not toxic to cells at concentrations sufficient to substantially increase induction. We decided to initially pursue a series of 3-deazapteridine analogs because of their strong oligonucleotide enhancing effects. The structures of three active compounds are shown in FIG. 1A (active compounds, UNC10217938A, UNC10217832A, UNC10217854A, hereafter abbreviated as 7938, 7832, 7854). Several compounds with closely related structures were inactive in the screen suggesting that activity was due to specific molecular interactions rather than general physical properties (data not shown).

Dose-Response, Specificity, and Cytotoxicity Relationships.

The confirmed hits were re-tested for SSO-mediated luciferase induction and for cytotoxicity in a 24 well format that allows for normalization based on cell protein. As seen in FIG. 1B the compounds strongly enhanced luciferase induction in HelaLuc705 cells when used in the 5-25 uM range and were substantially more effective and potent than Retro-1. For example, as compared to SSO alone, 7938 provided a 60-fold enhancement at 10 uM and 220-fold at 20 uM, in contrast to a 11-fold enhancement for 100 uM Retro-1. Mis-matched oligonucleotide had no effect in the presence of the hit compounds thus demonstrating specificity. As indicated in FIG. 1C, over 24 h only modest cytotoxicity was manifested below 20 uM. However, continuous protracted exposure to compound resulted in increased toxicity, as might be expected (data not shown). Pre-loading the cells with oligonucleotide did not alter the cytotoxicity of the hit compound (data not shown). These compounds displayed a rapid onset of action (data not shown), while the magnitude of the luciferase induction effect was only slightly less than that attained with use of a commercial cationic lipid transfection agent (data not shown). We also examined the ability of the compounds to enhance SSO-mediated splicing of an endogenous message (Bcl-X) and found them effective in this context (data not shown). When the amount of SSO was varied in the presence of a constant concentration of compound 7938, strong induction effects were observed with as little as 3 nM oligonucleotide (Supplementary Figure S6a). Thus, in summary, the hit compounds can strongly enhance the actions of splice switching oligonucleotides at compound concentrations that display only modest cytotoxicity.

Effects on Antisense and siRNA Oligonucleotides.

An important issue is whether the hit compounds directly affect the splicing process versus affecting the delivery of SSOs to the nucleus where splicing takes place. To address this issue we examined compound effects on the actions of an antisense oligonucleotide (ASO) that acts on pre-mRNA via RNase H in the nucleus, and on a siRNA that acts via the RISC complex in the cytosol. The ability to influence the actions of all three types of oligonucleotide would indicate that the hit compound affects delivery rather specific molecular events.

To test the influence of hit compounds on antisense we examined the ability to enhance 'knockdown' of the P-glycoprotein multidrug transporter (data not shown). Treatment of multi-drug resistant 3T3 cells with ASO alone had little effect, while use of a commercial cationic lipid transfection agent significantly enhanced the antisense action. Treatment of cells with 7938 also strongly enhanced ASO action to an extent comparable to that produced by the cationic lipid. In all cases only a portion of the cell population was affected as is typical in this model (59). When the amount of ASO was varied in the presence of a constant concentration of 7938, strong effects were observed with as little as 5 nM oligonucleotide (data not shown). Compounds 7832 and 7854 also enhanced the effects of an anti-MDR1 ASO but had no effect on mismatched oligonucleotides (data not shown). Strong antisense effects were attained at concentrations of enhancing compounds that displayed little cytotoxicity (data not shown).

Since conventional siRNA is unstable in cell culture media and is poorly taken up by cells, we used a cholesterol-conjugated siRNA to test effects of the enhancing compound (data not shown). Use of 7938 enhanced the ability of a siEGFP to reduce levels of EGFP in a cell line that stably expresses this reporter. A cholesterol-conjugated irrelevant control siRNA had no effect in the presence or absence of 7938.

These studies indicate that the hit compounds can enhance the pharmacological effects of several types of oligonucleotides that have distinct mechanisms of action. This supports the concept that these compounds act by influencing the intracellular trafficking and delivery of oligonucleotides rather than their direct actions.

Effects on Receptor-Targeted Oligonucleotide Conjugates.

Our laboratory has pursued the use of ligand-oligonucleotide conjugates to attain receptor-selective targeted delivery (Alam, M. R., et al., Bioconjugate chemistry, 22, 1673-1681 (2011), Ming, X., et al., Biomaterials, 34, 7939-7949 (2013), Nakagawa, O., et al., Bioconjugate chemistry, 25, 165-170 (2014)). Thus we were interested in whether our compounds would affect oligonucleotides that enter cells by receptor-mediated endocytosis. We used a previously described (Ming, X., et al., Biomaterials, 34, 7939-7949 (2013)) multivalent conjugate comprised of several RGD peptide-conjugated morpholino SSOs further conjugated via bioreversible links to serum albumin as a carrier. This conjugate displays efficient and selective uptake by cells that express RGD-binding integrins and modest but distinct splice correction effects (Ming, X., et al., Biomaterials, 34, 7939-7949 (2013)). We examined luciferase induction in αvβ3-expressing A375 melanoma cells that contain the Luc705 expression cassette. As seen in FIG. 2, treatment with 100 uM Retro-1 increased the ability of the conjugate to induce luciferase; however, 7938 at 5 or 10 uM had a far larger impact. Thus 7938 can substantially enhance effects of receptor targeted oligonucleotide conjugates. Additionally, this experiment illustrates that the compound can enhance effects of uncharged morpholino oligonucleotides as well as negatively charged oligonucleotides.

Effects on the Cellular Endomembrane System and on Subcellular Distribution of Oligonucleotide.

The results mentioned above suggested that the hit compounds affect the delivery of oligonucleotide to the cytosol and nucleus. Subsequent to cell uptake, oligonucleotides traffic through multiple endomembrane compartments (Varkouhi, A. K., et al., Journal of controlled release: official journal of the Controlled Release Society, 151, 220-228 (2011), Juliano, R. L., et al., Bioconjugate chemistry, 23, 147-157 (2012)). Our previous work and that of others has shown that typical antisense and SSO oligonucleotides primarily accumulate in late endosomes and lysosomes (Ming, X., et al., Biomaterials, 34, 7939-7949 (2013), Koller, E., et al., Nucleic Acids Res, 39, 4795-4807(2011), Ming, X. et al., Nucleic Acids Res, 41, 3673-3687 (2013)). Thus we were interested in studying the impact of the hit compounds on those organelles and on the intracellular distribution of oligonucleotide. We used baculovirus expression vectors for GFP chimeras of well-known marker proteins for distinct endomembrane compartments to visualize those compartments. This included GFP-Rab7a for late endosomes, GFP-LAMP1 for lysosomes and GFP-N-acetylgalactosaminyl-transferase 2 for Golgi apparatus (Doherty, G. J. et al., Annu Rev Biochem, 78, 857-902 (2009), Pfeffer, S. R., Current opinion in cell biology. 25: 414-19 (2013)). Transfection conditions were chosen so as to produce a mixture of untransfected cells and cells expressing the GFP chimeras in order to avoid overexpression artifacts.

Treatment of cells with 7938 had little effect on the compact organization of the Golgi apparatus (data not shown). The late endosome and lysosome compartments are more diffusely distributed but we did not observe major changes in the appearance of those compartments, nor in the number of well defined vesicles, upon treatment with 7938 (data not shown). Thus, at least at the descriptive level, 7938 did not cause substantial disruptions of the overall organization of the subcellular organelles examined. A SSO labeled at the 3' position with a TAMRA fluorophore was used to visualize 7938 effects on the subcellular distribution of oligonucleotide. Live cells were observed using a confocal microscope with environmental stage before and after addition of 7938 (images not shown). In cells that seem healthy and with normal morphology, treatment with 7938 led to a partial redistribution of oligonucleotide from endomembrane compartments to the nucleus. However, most of the oligonucleotide remained within endosomes. To further explore oligonucleotide distribution we quantitated the co-localization of GFP and TAMRA (Dunn, K. W., et al., Am J Physiol Cell Physiol, 300, C723-742 (2011), Zinchuk, V. et al., Current protocols in cell biology/editorial board, Juan S. Bonifacino . . . [et al.], Chapter 4:Unit 4.19 (2011)). As well, we quantitated the TAMRA fluorescence signal per unit area within the nucleus. As seen in FIG. 3A, exposure of cells to 7938 led to a major reduction in co-localization of the TAMRA-oligonucleotide with the late endosome marker Rab7, but had little effect on co-localization with the lysosomal marker LAMP-1. This suggests that 7938 primarily affects oligonucleotides in late endosomes. As seen in FIG. 3B, reduction of co-localization of the TAMRA and Rab7 signals was accompanied by an increase in accumulation of Tamra-oligonucleotide in the nucleus. Thus 3A-3D suggest that 7938 causes partial release of oligonucleotide from late endosomes to the cytosol followed by nuclear accumulation. In other studies we used a lysosomotropic dye to further probe possible effects of 7938 on lysosomes. Lysotracker Green primarily accumulates in the low pH lysosomal compartment; thus permeabilization of the lysosome membrane would disrupt the pH gradient and inhibit Lysotracker uptake by cells. As seen in Figure S10, concentrations of 7938 that are effective in enhancing oligonucleotide actions have almost no effect on Lysotracker Green accumulation suggesting that there are very limited effects on the lysosomal membrane. Another question is whether the enhancing compounds can also cause the release of other large molecules from endomembrane compartments. In an initial experiment we examined the effects of 7938 on the subcellular distribution of a fluorescent dextran having a molecular mass similar to that of an oligonucleotide. The dextran was partially released from endosomes subsequent to treatment with 7938 (data not shown).

In Vivo Studies.

In order to determine whether the strong enhancing effects of our hit compounds that were seen in cell culture would also be observed in vivo we tested the effectiveness of compound 7938 using a transgenic mouse model that is responsive to splice switching oligonucleotides (Sazani, P., et al., Nature biotechnology, 20, 1228-1233 (2002), Roberts, J., et al., Mol Ther, 14, 471-475 (2006)). In the EGFP654 transgenic line a reporter gene comprised of the EGFP coding sequence is interrupted by an aberrantly spliced intron. Effective delivery of an appropriate SSO to the nucleus of tissue cells will correct splicing leading to expression of normal EGFP mRNA and protein in that tissue. We visualized EGFP expression by fluorescence microscopy of tissue cryosections and evaluated correction of EGFP pre-mRNA splicing by RT-PCR. For the in vivo study we extrapolated our cell culture data to estimate a dose of 7938 that might be effective and non-toxic. The effect of a single administration of 7938 is likely to be transient, while the half-life of EGFP protein is substantially longer than that of its mRNA (Corish, P., et al., Protein engineering, 12, 1035-1040 (1999), Kudla, G., et al., PLoS biology, 4, e180 (2006)), thus we monitored RNA at 4 h and protein at 24 h after 7938 administration (data not shown). The systemic treatment with SS0623 followed by administration of 7938 produced distinct increases in EGFP fluorescence in liver, kidney and heart. Fluorescence was observed in the predominant cell type in each tissue including hepatocytes, kidney tubule cells, and cardiac muscle cells. In contrast, systemic treatment with SS0623 alone produced very modest increases in fluorescence in these tissues. A broader representation of the EGFP induction (data not shown) shows that skeletal muscle was not strongly affected and also that the combination of mis-matched oligonucleotide and 7938 had no effect. As seen in FIG. 4, correctly spliced EGFP message was found in liver, kidney and heart, paralleling the observations on tissue sections. The dose of 7938 used in this experiment did not result in acute toxicity to the EGFP654 mice as indicated by the lack of significant changes in blood chemistry parameters (data not shown). Additionally, a 7 day toxicity study done in C57BL/6 mice at doses that overlap those used in the experiment of FIG. 4 showed no significant evidence of toxicity (data not shown).

The foregoing is illustrative of the present invention, and is not to be construed as limiting thereof. The invention is defined by the following claims, with equivalents of the claims to be included therein.

That which is claimed is:

1. A method of administering an oligonucleotide of interest to a cell, the method comprising:
   concurrently administering an active agent to said cell in an amount effective to increase the delivery and/or increase the activity of said oligonucleotide in said cell;
   wherein said active agent is a compound of Formula I:

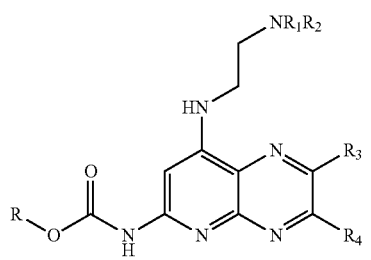

wherein:
   R is ethyl or a linking group;
   $R_1$ is methyl or a linking group;
   $R_2$ is methyl;
   $R_3$ and $R_4$ are each independently H, lower alkyl; lower alkoxy, halo, amino, aryl, or heteroaryl;
   or a pharmaceutically acceptable salt thereof; and
wherein the oligonucleotide is not targeted to a bacterial pathogen.

2. The method of claim 1, wherein said cell is a mammalian cell.

3. The method of claim 1, wherein said method is carried out in vitro or in vivo.

4. The method of claim 1, wherein said method is carried out by administering said oligonucleotide to a subject in need thereof, and concurrently administering said active agent to said subject.

5. The method of claim 1, wherein said active agent is administered after said oligonucleotide.

6. The method of claim 1, wherein said oligonucleotide is single stranded.

7. The method of claim 1, wherein said oligonucleotide is from 2, 4, 6 or 8 to 100 or 200 nucleotides in length.

8. The method of claim 1, wherein said oligonucleotide is negatively charged.

9. The method of claim 1, wherein said oligonucleotide is an antisense oligonucleotide.

10. The method of claim 1, wherein said oligonucleotide is a splice switching oligonucleotide.

11. The method of claim 1, wherein said active agent is selected from the group consisting of:

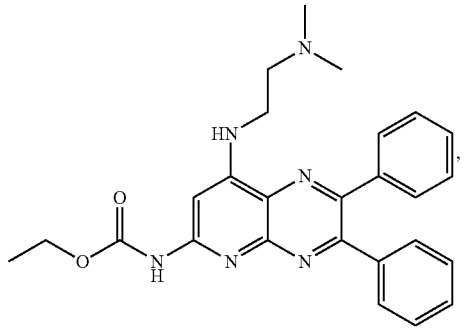

UNC10217938A and pharmaceutically acceptable salts thereof.

12. A composition comprising:
   (a) an oligonucleotide and;
   (b) an active agent, in combination in
   (c) a pharmaceutically acceptable carrier;
   wherein said active agent is a compound of Formula:

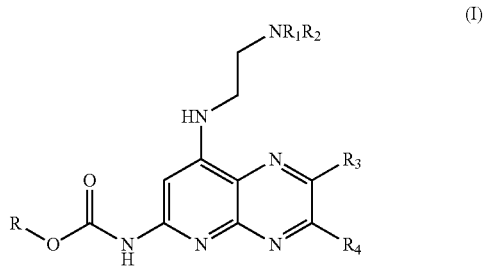

wherein:
   R is ethyl or a linking group;
   $R_1$ is methyl or a linking group;
   $R_2$ is methyl;

$R_3$ and $R_4$ are each independently H, lower alkyl; lower alkoxy, halo, amino, aryl, or heteroaryl;

or a pharmaceutically acceptable salt thereof; and
wherein the olignucleotide is not targeted to a bacterial pathogen.

13. The composition of claim 12, wherein said oligonucleotide is single stranded.

14. The composition of claim 12, wherein said oligonucleotide is from 2, 4, 6 or 8 to 100 or 200 nucleotides in length.

15. The composition of claim 12, wherein said oligonucleotide is negatively charged.

16. The composition of claim 12, wherein said oligonucleotide is an antisense oligonucleotide.

17. The composition of claim 12, wherein said oligonucleotide is a splice switching oligonucleotide.

18. The composition of claim 12, wherein said active agent is selected from the group consisting of:

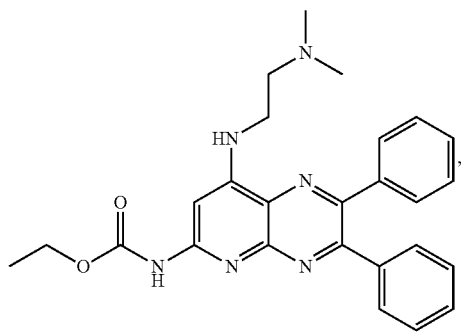

UNC10217938A and pharmaceutically acceptable salts thereof.

19. A composition comprising:
(a) an oligonucleotide and;
(b) an active agent, in combination in
(c) a pharmaceutically acceptable carrier;
wherein said active agent is selected from the group consisting of:

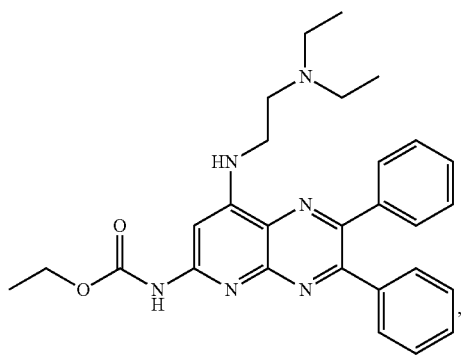

UNC10217832

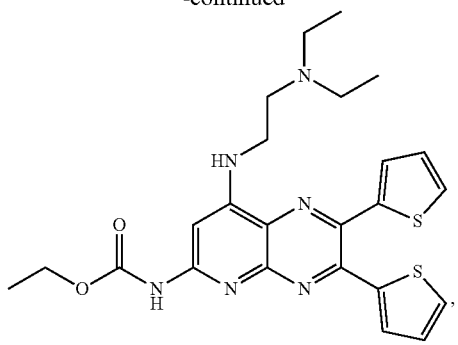

UNC10217854 and pharmaceutically acceptable salts thereof; and
wherein the oligonucleotide is not targeted to a bacterial pathogen.

20. A method of administering an oligonucleotide of interest to a cell, the method comprising:
concurrently administering an active agent to said cell in an amount effective to increase the delivery and/or increase the activity of said oligonucleotide in said cell;
wherein said active agent is selected from the group consisting of:

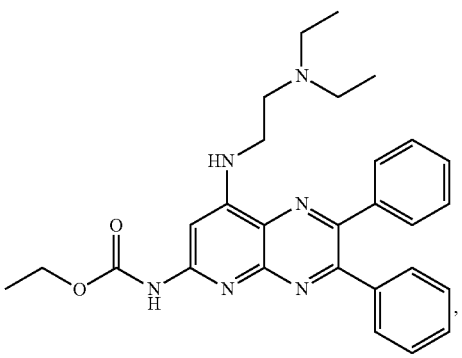

UNC10217832

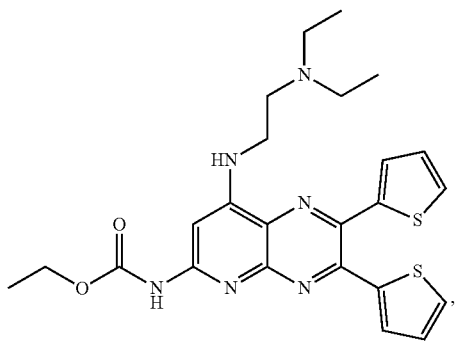

UNC10217854 and pharmaceutically acceptable salts thereof; and
wherein the oligonucleotide is not targeted to a bacterial pathogen.

* * * * *

UNITED STATES PATENT AND TRADEMARK OFFICE
CERTIFICATE OF CORRECTION

PATENT NO. : 10,266,823 B2  
APPLICATION NO. : 15/318260  
DATED : April 23, 2019  
INVENTOR(S) : Juliano et al.

Page 1 of 1

It is certified that error appears in the above-identified patent and that said Letters Patent is hereby corrected as shown below:

In the Specification

Column 23, Line 22: Please correct "SSO0623" to read -- SSO623 --

Column 23, Line 58: Please correct "SS0623" to read -- SSO623 --

Column 25, Line 16: Please correct "C02" to read -- CO2 --

Column 25, Line 40: Please correct "SS0623" to read -- SSO623 --

Column 25, Line 58: Please correct "SS0623" to read -- SSO623 --

Column 30, Line 3: Please correct "SS0623" to read -- SSO623 --

Column 30, Line 8: Please correct "SS0623" to read -- SSO623 --

In the Claims

Column 32, Line 50, Claim 12: Please correct "Formula:" to read -- Formula I: --

Signed and Sealed this  
Twenty-seventh Day of August, 2019

Andrei Iancu  
*Director of the United States Patent and Trademark Office*

SEQUENCE LISTING

```
<160> NUMBER OF SEQ ID NOS: 6

<210> SEQ ID NO 1
<211> LENGTH: 23
<212> TYPE: DNA
<213> ORGANISM: Mus musculus

<400> SEQUENCE: 1
aagctggccc tggacatgga gat                                           23

<210> SEQ ID NO 2
<211> LENGTH: 20
<212> TYPE: DNA
<213> ORGANISM: Artificial
<220> FEATURE:
<223> OTHER INFORMATION: Splice switching oligonucleotide sequence

<400> SEQUENCE: 2
gttattcttt agaatggtgc                                               20

<210> SEQ ID NO 3
<211> LENGTH: 20
<212> TYPE: DNA
<213> ORGANISM: Artificial
<220> FEATURE:
<223> OTHER INFORMATION: Mismatch control oligonucleotide sequence

<400> SEQUENCE: 3
gtaattattt ataatcgtcc                                               20

<210> SEQ ID NO 4
<211> LENGTH: 20
<212> TYPE: DNA
<213> ORGANISM: Artificial
<220> FEATURE:
<223> OTHER INFORMATION: Anti-MDR1 antisense oligonucleotide sequence

<400> SEQUENCE: 4
ccatcccgac ctcgcgctcc                                               20
```

```
<210> SEQ ID NO 5
<211> LENGTH: 20
<212> TYPE: DNA
<213> ORGANISM: Artificial
<220> FEATURE:
<223> OTHER INFORMATION: Bcl-x pre-mRNA splice switching oligonucleotide
      sequence

<400> SEQUENCE: 5
tggttcttac ccagccgccg                                                 20

<210> SEQ ID NO 6
<211> LENGTH: 19
<212> TYPE: DNA
<213> ORGANISM: Artificial
<220> FEATURE:
<223> OTHER INFORMATION: siRNA sequence

<400> SEQUENCE: 6
gccacaacgu cuauaucau                                                  19
```